(12) United States Patent
Kimmig et al.

(10) Patent No.: US 12,324,911 B2
(45) Date of Patent: Jun. 10, 2025

(54) IMPLANTABLE ELECTRICAL CONTACT ARRANGEMENT

(71) Applicant: Neuroloop GmbH, Freiburg (DE)

(72) Inventors: Fabian Kimmig, Teningen (DE); Tim Boretius, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 302 days.

(21) Appl. No.: 17/608,673

(22) PCT Filed: Apr. 30, 2020

(86) PCT No.: PCT/EP2020/062018
§ 371 (c)(1),
(2) Date: Nov. 3, 2021

(87) PCT Pub. No.: WO2020/225090
PCT Pub. Date: Nov. 12, 2020

(65) Prior Publication Data
US 2022/0212000 A1   Jul. 7, 2022

(30) Foreign Application Priority Data

May 3, 2019   (DE) ................. 10 2019 206 388.8

(51) Int. Cl.
*A61N 1/05*   (2006.01)
*A61B 5/00*   (2006.01)
*A61B 5/294*   (2021.01)

(52) U.S. Cl.
CPC ............ *A61N 1/0556* (2013.01); *A61B 5/294* (2021.01); *A61B 5/4041* (2013.01);
(Continued)

(58) Field of Classification Search
None
See application file for complete search history.

(56) References Cited

U.S. PATENT DOCUMENTS

| 5,653,742 A | * | 8/1997 | Parker ................. A61D 7/00 607/116 |
| 5,919,220 A | | 7/1999 | Stieglitz et al. |

(Continued)

FOREIGN PATENT DOCUMENTS

| DE | 202010015346 U1 | 3/2011 |
| EP | 0843574 B1 | 12/1999 |

(Continued)

OTHER PUBLICATIONS

International Search Report for PCT/EP2020/062018, mailed Aug. 11, 2020; English translation submitted herewith (4 pgs.).

*Primary Examiner* — Carl H Layno
*Assistant Examiner* — Manolis Pahakis
(74) *Attorney, Agent, or Firm* — Fitch, Even, Tabin & Flannery LLP

(57) ABSTRACT

An implantable electrical contact arrangement comprising at least one electrode element entirely integrated into a carrier substrate of a biocompatible, electrically insulating material, and at least one freely accessible electrode surface enclosed by the biocompatible, electrically insulating carrier substrate. Within at least one space of the carrier substrate, which does not contain an electrode element, the carrier substrate surrounds at least one space containing at least one material with a modulus of elasticity differing from a modulus of elasticity of the material of the carrier substrate.

23 Claims, 1 Drawing Sheet

(52) U.S. Cl.
CPC .......... *A61B 5/6847* (2013.01); *A61B 5/6877* (2013.01); *A61B 5/6884* (2013.01)

(56) References Cited

U.S. PATENT DOCUMENTS

| | | | | |
|---|---|---|---|---|
| 9,370,660 | B2* | 6/2016 | Gross | A61N 1/36135 |
| 9,907,950 | B1* | 3/2018 | Perryman | A61N 1/3756 |
| 11,628,297 | B2* | 4/2023 | Vachicouras | A61N 1/05 |
| | | | | 607/129 |
| 12,226,628 | B2* | 2/2025 | Searfoss | A61N 1/0556 |
| 2008/0004673 | A1* | 1/2008 | Rossing | A61N 1/05 |
| | | | | 607/44 |
| 2008/0051667 | A1* | 2/2008 | Goldreich | G16H 40/67 |
| | | | | 600/481 |
| 2011/0122486 | A1 | 5/2011 | Busch | |
| 2012/0035615 | A1* | 2/2012 | Koester | A61B 17/3468 |
| | | | | 607/137 |
| 2012/0296444 | A1* | 11/2012 | Greenberg | A61N 1/0531 |
| | | | | 607/152 |
| 2013/0150940 | A1* | 6/2013 | Wilson | A61B 5/4094 |
| | | | | 607/118 |
| 2014/0188202 | A1* | 7/2014 | Zarembo | A61N 1/0556 |
| | | | | 607/118 |
| 2016/0120472 | A1* | 5/2016 | Kub | C23C 16/405 |
| | | | | 216/13 |
| 2017/0087350 | A1 | 3/2017 | Skiba | |
| 2017/0173340 | A1* | 6/2017 | Gupte | A61N 1/36114 |
| 2017/0202467 | A1* | 7/2017 | Zitnik | A61N 1/3787 |
| 2017/0319846 | A1 | 11/2017 | Plachta et al. | |
| 2018/0056074 | A1* | 3/2018 | Clark | A61N 1/36139 |
| 2019/0217082 | A1* | 7/2019 | Modi | A61B 5/24 |
| 2019/0275328 | A1* | 9/2019 | Zitnik | A61N 1/3756 |
| 2019/0351214 | A1* | 11/2019 | Boretius | A61N 1/05 |
| 2019/0388680 | A1* | 12/2019 | Jain | A61N 1/0556 |
| 2022/0184387 | A1* | 6/2022 | Searfoss | A61N 1/0556 |
| 2022/0296884 | A1* | 9/2022 | Jeong | A61N 1/0558 |

FOREIGN PATENT DOCUMENTS

| | | |
|---|---|---|
| EP | 3204105 B1 | 8/2018 |
| WO | 2017/181027 A1 | 10/2017 |

* cited by examiner

IMPLANTABLE ELECTRICAL CONTACT ARRANGEMENT

CROSS-REFERENCE TO RELATED APPLICATIONS

Reference is made to International Application No. PCT/EP2020/062018, filed Apr. 30, 2020, which claims priority to German Patent Application No. 10 2019 206 388.8, filed May 3, 2019, the contents of which are incorporated herein by reference in their entirety.

BACKGROUND OF THE INVENTION

Field of the Invention

The invention relates to an implantable electrical contact arrangement which comprises at least one electrode element arrangement which is otherwise entirely integrated into a carrier substrate produced of a biocompatible, electrically insulating material, and at least one freely accessible electrode surface enclosed directly or indirectly by the biocompatible, electrically insulating carrier substrate.

Description of the Prior Art

Implantable electrical contact arrangements are used for at least one of applying electrical signals to and tapping electrical signals from intracorporeal tissue surfaces, in particular on surfaces of vessel, muscle or nerve fibers. A particular challenge in the intracorporeal positioning of such implantable electrical contact arrangements is to gently apply the contact arrangement as immovably as possible on an intracorporeal surface without impairing or irritating the latter in the long-term. However, this makes great demands on the fixation of the implant side of the electrical contact arrangement on the respective tissue surface. Because of intracorporeal temperature and pressure changes, the tissue surface undergoes movements and shape changes, which should not, or as far as possible should not, be impeded by the medical implant. At the same time, the local surface contact between the electrode surface of an electrode applied on the implant side should be formed with an as unchangeable as possible defined surface contact pressure which should guarantee constant electrical transmission properties.

In addition to different forms of embodiments of implantable electrode arrangements, extraneuronal, and cuff configured electrodes, are applied circularly around a nerve fiber bundle for allowing electroneural stimulations to be carried out as well as the local tapping of electroneural signals along a nerve fiber bundle. Due to the circular open wrapping of the cuff electrode, the latter can mould itself radially from outside onto the nerve fiber bundle and at the same time follow radial changes in the shape of the nerve fiber bundle.

The electrode elements of an implantable electrical contact cuff electrode, which are in contact with the nerve fiber bundle, are applied to a biocompatible, electrically insulating, sheet carrier substrate which in a planar state can, through at least one of surface wrapping and surface curvature assume the shape of a straight hollow cylinder. In this state of the cuff electrode, the freely accessible electrode surfaces of the electrode elements are located on the inside of the carrier substrate which is shaped into a hollow cylinder, and in the implanted state can rest directly on the epineurium of the nerve fiber bundle.

An electrode is described in EP 0 843 574 B1, in which the sheet carrier substrate is configured to form an interdigital finger structure. Through bending of the sheet, the flexible finger sections take on the shape of a straight hollow cylinder with the cylinder diameter being flexibly variable through the respective finger sections that end freely and variably interlock. To produce and support the hollow cylinder shape, the sheet carrier substrate substance has at least one layer of shape-memory material or a mechanically pre-stressed material layer.

An alternative design for producing an implantable cuff electrode arrangement is described in EP 3 204 105 B1. In this case, the cuff electrode, which is configured as an electrode wrap, comprises a sheet of a flexible, biocompatible carrier substrate, preferably in the form of a polyimide film on the one carrier substrate upper side of which an electrode arrangement composed of individual electrode elements is applied. The individual electrodes of the electrode arrangement come into direct surface contact with the epineurium of the nerve fiber bundle, particularly as the carrier substrate rolls up by itself into a straight cylindrical wound shape through appropriately incorporating mechanical pre-stressing into the film. Through the winding, which is open at one end, wrapped layers of the sheet of the carrier substrate which slide loosely on each other are formed, at least in sections, through which individual diameter variation of the hollow cylindrical cuff electrode arrangement in contact around the nerve fiber bundle is possible.

The contact pressure in which the electrode surfaces are each in contact with the epineurium of the nerve fiber bundle, is essentially determined by the elastic material properties of the entire sheet of the carrier substrate.

DE 20 2010 015 346 U1 discloses electrode arrangements in which among the electrodes within a strand-shaped substrate, a one-piece nitinol strip projects through the entire substrate for shaping purposes. The nitinol band has a modulus of elasticity which differs from the modulus of elasticity of the carrier substrate and has a function that supports the shape of the electrode assembly as a spine.

US published patent application 2008/0004673 discloses an elastically deformable electrode cuff, into which for example nitinol, is incorporated for shaping purposes.

SUMMARY OF THE INVENTION

The invention is an implantable electrical contact, which comprises at least one electrode element arrangement, which is otherwise entirely integrated into a carrier substrate produced from a biocompatible, electrically insulating material, and at least one freely accessible electrode surface is enclosed directly or indirectly by the biocompatible, electrically insulating carrier substrate so that the contact pressure with which the at least one electrode surface lies on an intracorporeal tissue surface is individually adjustable without changing, or essentially changing, the carrier substrate in terms of its spatial dimensions, in particular in terms of the carrier substrate thickness. It should be possible to individually chose the contact pressure on the surface along which the carrier substrate contacts an intracorporeal tissue surface dependent on the location along the contacting carrier substrate surface.

Turning away from an obvious variation, above all increasing the material thickness of the sheet carrier substrate causes greater local material rigidity and an associated increase in the surface contact forces. The implantable electrical contact arrangement according to the invention has a sub-space which does not contain the at least one electrode element arrangement and in which the carrier substrate directly or indirectly surrounds at least one space containing at least one material having a modulus of elasticity differing from a modulus of elasticity assigned of the material of the carrier substrate.

The invention fundamentally permits individual setting or specification of the surface elasticity or surface stiffness of the sheet carrier substrate, without changing, or essentially changing, the thickness of the sheet carrier substrate. In particular, in this way, implantable electrical contact arrangements can be produced in which the electrode surfaces are pressed onto an intracorporeal tissue surface with a higher pressing force in comparison with the remaining sheet carrier substrate.

In this manner, on one hand it is ensured that electrical contact with the tissue takes place durably, stably and with constant electrical properties, which in the remaining region, for the purposes of fixing, the sheet of the carrier substrate is in contact with the nerve fiber bundle with a sufficiently low contact force in a way that is not harmful to the tissue. To this end, for filling the space, at least one material is selected which has a higher modulus of elasticity in comparison with the modulus of elasticity of the material from which the carrier substrate is made. In a corresponding manner, the surface stiffness can be locally reduced in regions of the carrier substrate, so that for filling the space, at least one material is selected which has a lower modulus of elasticity in comparison with the modulus of elasticity of the material of which the carrier substrate is made. Depending on the material selection as well as the provision of spaces within the sheet of the carrier substrate, any desired stiffness gradient can be produced within the carrier substrate.

In a preferred embodiment, the sheet of the carrier substrate comprises a neutral fiber separating a sub-space of the carrier substrate containing the at least one electrode element arrangement from the sub-space of the carrier substrate containing the at least one space.

The at least one space is completely surrounded by the biocompatible, electrically insulating material of the carrier substrate. Dimensionally the at least one space is orientated relative to the longitudinal direction of the sheet to be dimensioned very much smaller than the sheet-like carrier substrate. This enables problem-free intracorporeal use of the implantable electrical contact arrangement according to the invention, particularly as the at least one material that is implemented in the carrier substrate is not in contact with the intracorporeal environment.

Preferably, in a direction of an orthogonal projection onto the electrode surface, the at least one space overlaps, at least partially, and preferably completely, the electrode surface. In this way it is ensured that at least the carrier substrate area containing the electrode surface is locally pressed against the intracorporeal tissue surface with an increased or individually adapted contact force.

Typically, the sheet of the carrier substrate is made of a polymer, for example polyimide, liquid crystal polymer (LCP), parylene or PDMS. Typically, such materials have a modulus of elasticity of between 1 to 2 GPa. When using a metallic material for filling the at least one space, significant stiffness gradient of the metallic material can be incorporated within the sheet of the carrier substrate. The following table shows the moduli of elasticity belonging to the individual metallic materials:

| Material | Modulus of elasticity in GPa |
| --- | --- |
| Gold | 78 |
| Copper | 100 to 130 |
| Aluminium | 70 |
| Nickel | 195 to 205 |
| Ceramic | 160 to 440 |
| Graphene | approximately 1000 |

In addition to the above solid substances, which are not exhaustively named in the table, which all contribute to local stiffening of the carrier substrate made of polymer, other materials having a lower modulus of elasticity than the modulus of elasticity of the carrier substrate, can be inserted or enclosed in the at least one space within the carrier substrate. For example, gels, liquids or also gases which can be inserted within the carrier substrate, are also suitable. In addition, when using gases or liquids, their modulus of elasticity can be co-determined by the pressure of the respective gaseous or liquid material for filling the at least one space within the sheet of the carrier substrate.

In a further preferred embodiment, within the at least one space, at least two materials with different moduli of elasticity are incorporated, preferably as a layer sequence of two solid materials, preferably in the form of two different metal layers. Through the combination of several substances with differing moduli of elasticity, it is possible to randomly set graduated modulus of elasticity profiles within the carrier module.

In a further embodiment, preferably for local stiffening of the carrier substrate, the material filling the at least one space is with a transducer material, which for the purpose of changing at least one of its shape and elasticity can be modified through an external effect, for example, through an external energy field. Suitable transducer materials are materials such as, for, bimetals, shape-memory alloys, piezo ceramics, electrostrictive ceramics, magnetoscriptive alloys, electro- or magnetorheological fluids or similar materials.

The implantable electrical contact arrangement typically has a flat carrier substrate which in terms of shape and size is suitably dimensioned for application to an intracorporeal tissue or nerve fiber bundle region. Typical area sizes for the carrier substrate, which, depending on the application, can be at least one of folded and wrapped in a singly or multiply overlapping manner, are between a few mm$^2$ and a few cm$^2$, for example between 4 mm$^2$ and 20 cm$^2$, and preferably from 10 mm$^2$ to 6 cm$^2$. The sheet of the carrier substrate has a substrate thickness of a few μm to several hundred μm, for example from 2 μm to 650 μm, and preferably 10 μm to 100 μm.

The at least one space, which is completely hermetically surrounded by the carrier substrate material and preferably has a cubic or cuboid shape, is dimensioned to be very much smaller than the dimension of the carrier substrate in its longitudinal direction. Maximally, the least one space encloses a volume of 17 mm$^3$. The space filled with a material; which has a modulus of elasticity differing from the modulus of elasticity of the carrier substrate, can only locally influence the properties of the carrier substrate in the area around the space. Because of the small dimensions of the at least one space in relation to the size of the carrier substrate, the material contained in the space does not exert a supporting force affecting the entire spatial shape of the carrier substrate. Even in the case of spaces that are distributed within the carrier substrate and are filled with at least one material and are each arranged at a distance from one another in an insular manner, the spatial areas with moduli of elasticity that are different from the modulus of elasticity of the carrier substrate in sections act to stiffen or soften the modulus of elasticity of the carrier substrate, but not defining the spatial shape, since the spaces are unable to develop a coherent supporting effect.

Thus, one example of an embodiment has first spaces, each filled with at least one material, that are distributed in an array along a first straight line or along a first plane each at a distance from each other within the carrier substrate.

In a further embodiment, in addition to the above first surface and second spaces are each filled with at least one material distributed along a second straight line or along a second plane each spaced at a distance from each other within the carrier substrate. Preferably, the first and the second straight line, or the first and the second plane are orientated parallel to each other.

In addition to the first and the second spaces filled with at least one material, a further embodiment has spaces each filled with at least one material that are distributed along a further straight line or along a further plane each spaced at a distance from each other within the carrier substrate.

With such spaces filled with a material, a sheet of carrier substrate regions having at least one of individually defined hardnesses and stiffnesses can be specified.

Particularly in the case of a cuff electrode that can be wrapped around a nerve fiber bundle, the carrier substrate region which is in direct contact with at least one of the nerve fiber bundle and the wrappings of the carrier substrate located close to the nerve fiber bundle can be designed with an area stiffness that is as low as possible, in that in this region of the carrier substrate there are no spaces filled with a material, or there are only spaces filled with a material having a modulus of elasticity that is significantly lower than the modulus of elasticity of the carrier substrate material. Incorporated in the radially adjoining carrier substrate region of the cuff electrode are spaces filled with material having a modulus of elasticity which is selected to be greater than the modulus of elasticity of the carrier substrate material. In this way an increased radially acting external contact pressure can be exerted on the inner carrier substrate layers.

BRIEF DESCRIPTION OF THE DRAWINGS

The invention will be described below, without restricting the invention, by way of examples of embodiment with reference to the drawings. Here.

DETAILED DESCRIPTION OF THE INVENTION

Figure 1A:
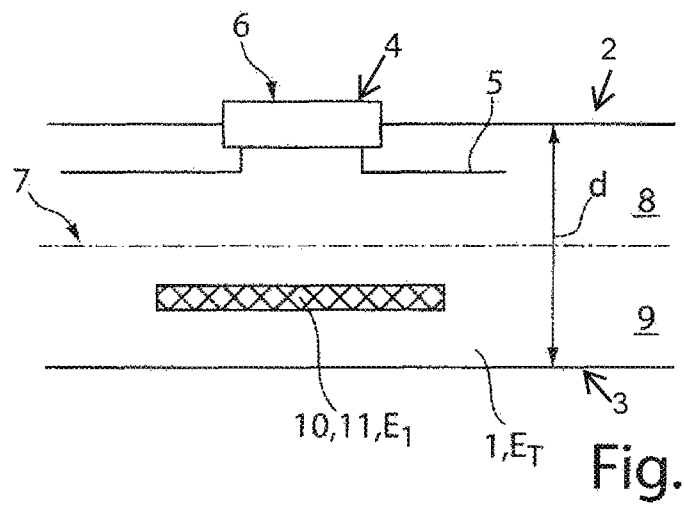
FIG. 1a, b, and c each show a longitudinal section through a carrier substrate with an electrode arrangement and at least one space.

FIG. 1a shows a longitudinal section through a sheet of carrier substrate 1, preferably in the form of polyimide film, with a carrier substrate upper side 2, and opposite this, a carrier substrate underside 3. Embedded within the carrier substrate 1 is an electrode which comprises at least one electrode element 4 contacted via electrical supply and outlet leads 5 extending within the carrier substrate 1. The electrode element 4 comprises a freely accessible electrode surface 6. Not necessarily, but advantageously, the electrode element 4 projects beyond the carrier substrate upper side 2, which in the implanted state is orientated towards an intracorporeal tissue surface, (not shown) so that the electrode surface 6 comes into surface contact with the tissue surface.

The sheet of the carrier substrate 1 comprises a neutral fiber 7, which separates the carrier substrate 1 into an upper sub-space 8 and a lower sub-space 9. The upper sub-space 8 contains the electrode, whereas the lower sub-space of the carrier substrate 1 contains at least one space 10, which is completely enclosed by the material of the carrier substrate 1 and in which at least one material 11 is contained which has a modulus of elasticity E1 differing from the modulus of elasticity $E_t$ of the carrier substrate 1.

In the example embodiment shown in FIG. 1a, there is an orthogonal projection onto the carrier substrate upper side 2 and the space 10 is locally arranged to completely overlap underneath the electrode element 4.

A preferred material selection is the use of a metallic substance 11 within the space 10, which is preferably in the form of a one-piece metallic layer, that is completely surrounded by the biocompatible, electrically insulating material of the carrier substrate 1 in an all-encompassing manner. The metallic substance 11 can locally stiffen the carrier substrate 1, so that when the carrier substrate is designed as a cuff electrode, a local increase in the contact pressure is achieved in the region of the electrode element 4 on an intracorporeal tissue surface, which is preferably a nerve fiber bundle. The additional implanting or integration of a material 11 within the space 10 is not associated with an increase in the carrier substrate thickness d.

The spatial and dimentional arrangement, of the space 10 within the carrier substrate can be diversely selected.

Figure 1B:
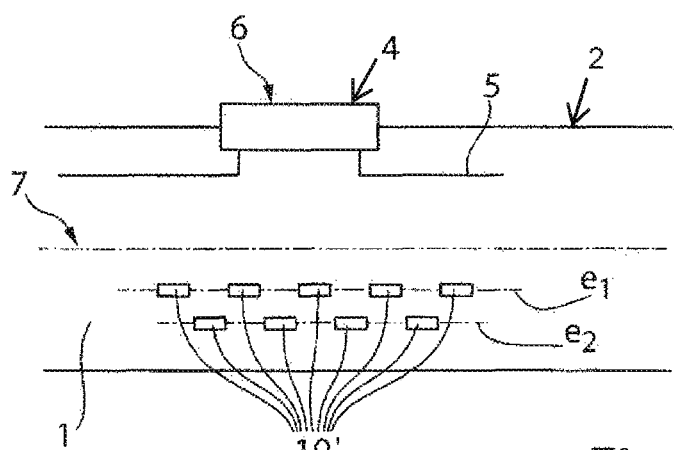

FIG. 1b illustrates an alternative embodiment that has individual spaces 10' within the carrier substrate 1 which are all uniformly filled with one material 11 or each are filled with different materials, depending on the desired setting of the stiffness of the carrier substrate 1 in the region of the at least one electrode element 4. In FIG. 1b, the spaces 10' are arranged along a plane e1 running in parallel to the neutral fiber 7. Also alternative arrangement patterns of the individual spaces 10' may be used, for example within two or more planes e1, e2 etc. running parallel to each other.

Figure 1C:
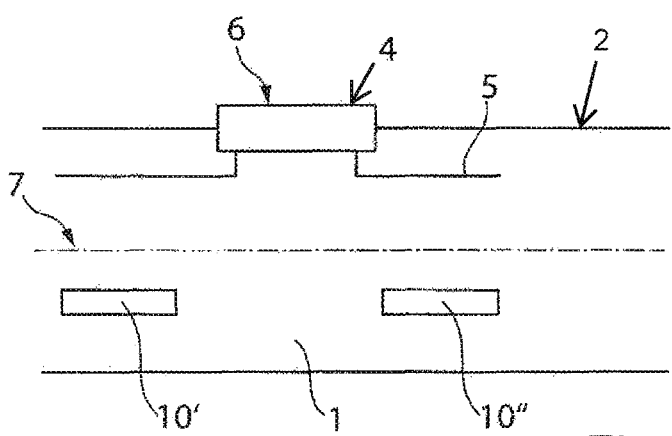

FIG. 1c illustrates a further example of embodiment with at least two spaces 10' and 10", which each orthogonally project onto the carrier substrate upper side 2 and are applied laterally next to the electrode 4. In this case, when the spaces 10' are filled with a material having a higher modulus of elasticity than the modulus of elasticity of the carrier substrate 1, the carrier substrate 1 has a lower stiffness in the region of the electrode arrangement than in regions of the carrier substrate which laterally are adjoining it.

Common to all embodiments is the fact that as a result of the provision within the carrier substrate 1 of a space, or spaces, which are each filled with at least one material, without an increase in the thickness of the sheet carrier substrate, that produces randomly stiffness gradients can be defined within the carrier substrate 1. In addition, because of the free selection of materials for filling the individual spaces, which in addition to solids can also include gaseous or, in particular, liquid or gel-like substances. The surface stiffness behavior of the entire carrier substrate can be finished to have an individual and finely-controlled manner.

Also possible is the use of fabric or fiber materials, which can be integrated in a locally limited way within the carrier substrate individually or in layers. For example, in the case of a fabric layer, this can be surrounded like a matrix by the biocompatible, electrically non-conductive material of the carrier substrate.

According to the invention at least one space within the carrier substrate is filled with a material having the modulus of elasticity differing from the modulus of elasticity of the carrier substrate, which also compensates for mechanical stresses that occur within the carrier substrate as a result of the integration of the electrode arrangement inside the carrier substrate. Such mechanical stresses can lead to excessive material stresses within the carrier substrate and ultimately restrict the lifespan of the implantable electrical contact arrangement. More particularly, designing the implantable electrical contact arrangement in the form of a known cuff electrode results in material-intrinsic mechanical stresses, which can be completely, or at least largely compensated by way of at least one material-filled space within the carrier substrate of the invention.

LIST OF REFERENCE NUMBERS

1 Carrier substrate
2 Upper side of carrier substrate
3 Lower side of carrier substrate
4 Electrode element
5 Electrical supply and outlet lead
6 Electrode surface
7 Neutral fiber
8 Sub-space containing the electrode element
9 Sub-space containing the at least one space
10, 10', 10" Space
11 Material
e1, e2 Arrangement plane for the spaces
d Sheet thickness of the carrier substrate
E1 Modulus of elasticity of the material
$E_T$ Modulus of elasticity of the carrier substrate

The invention claimed is:

1. An implantable electrode contact arrangement configured for implantation into a patient, comprising:
a film of biocompatible electrical insulating material configured for implantation into the patient, the film enclosing at least one space and a mechanical neutral fiber dividing the film into an upper part and a lower part;
at least one electrode integrated into the upper part of the film, the at least one electrode including a freely accessible contact surface for contact with an intracorporeal nerve bundle;
a transducer material within the at least one space, wherein the transducer material provides local stiffening, has a modulus of elasticity that is higher than the modulus of elasticity of the film, and changes shape or elasticity in response to an external energy field; and wherein
the at least one space is formed below the neutral fiber, an orthogonal projection of the at least one space onto the contact surface at least partially overlaps the contact surface, a longitudinal length of the at least one space is smaller than a longitudinal length of the film, the upper part of the film is free of the transducer material, and the electrode contact arrangement is configured so that a contact pressure applied by the contact arrangement to the intracorporeal nerve bundle is locally elevated at the at least one contact surfaces.

2. The implantable electrode contact arrangement in accordance with claim 1, wherein the material is selected from the group of materials consisting of a bimetal, a shape-memory alloy, a piezo ceramic, an electrostrictive material ceramic, a magnetostrictive alloy, and an electro and magnetorheological fluid.

3. The implantable electrode contact arrangement in accordance with claim 2, wherein the modulus of elasticity of the material in the at least one space is higher than the modulus of elasticity of the material of the sheet which causes increased stiffness of the sheet in a vicinity of the spaces.

4. The implantable electrode contact arrangement in accordance with claim 1, wherein upon implantation, the accessible electrode surface is oriented towards an intracorporeal tissue surface of the patient and the accessible electrode surface electrically contacts the intracorporeal tissue surface to establish the electrical contact between the implanted accessible surface and the accessible electrode surface and applies a locally elevated controlled contact pressure to the nerve bundle.

5. The implantable electrode contact arrangement in accordance with claim 1, wherein upon implantation an orthogonal projection of a side of the at least one space completely overlaps the accessible electrode surface.

6. The implantable electrode contact arrangement in accordance with claim 1, wherein the modulus of elasticity of the material in the at least one space is higher than the modulus of elasticity of the sheet of biocompatible electrical insulating material which causes increased stiffness of the sheet in a vicinity of the at least one space.

7. The implantable electrical contact arrangement according to claim 6, wherein the at least one space contains at least two materials each having a different modulus of elasticity.

8. The implantable electrode contact arrangement in accordance with claim 1, wherein the at least one space contains layers of two solid materials.

9. The implantable electrode contact arrangement in accordance with claim 1, wherein the at least one space contains materials which each have a different modulus of elasticity creating a graduated modulus of elasticity profile within the electrode contact arrangement.

10. The implantable electrode arrangement in accordance with claim 1, wherein:
the sheet of biocompatible electrical insulating material, when implanted, extends in a longitudinal direction and the at least one space has a length in the longitudinal direction which is smaller than a length of the sheet in the longitudinal direction.

11. The implantable electrical contact arrangement according to claim 1, comprising:
the mechanical neutral fiber within the sheet of biocompatible electrical insulating material located in a region of the at least one sheet separates the at least one space from the accessible electrode.

12. The implantable electrical contact arrangement according to claim 1, wherein upon implantation, the at least one space has a surface projecting orthogonally toward the accessible electrode which at least partially overlaps the accessible electrode and presses the electrode against the intracorporeal surface of the nerve bundle.

13. The implantable electrical contact arrangement according to claim 1, wherein the biocompatible electrical insulating material comprises a polymer selected from the group consisting of: polyimide, liquid crystal polymer (LCP), parylene and PDMS.

14. The implantable electrical contact arrangement according to claim 1, wherein:
the biocompatible electrical insulating material comprises a gaseous, a liquid or a solid material.

15. The electrical contact arrangement according to claim 1, wherein:
the at least one space varies in volume along the longitudinal dimension of the sheet biocompatible electrical insulating material.

16. The implantable electrical contact arrangement according to claim 1, wherein:
   the at least one space encloses a spatial volume having a maximum of 17 mm$^3$.

17. The implantable electrical contact arrangement according to claim 16, wherein:
   the at least one space is filled with at least one material, is in an array extending in a line or along a plane and each space is separated from any other space within a carrier substrate of the film.

18. The implantable electrical contact arrangement according to claim 17, comprising:
   additional spaces are filled with at least one material and extend in a second line within a second plane separated from the first plane within the sheet of the biocompatible electrical insulting material.

19. The implantable electrical contact arrangement according to claim 18, wherein:
   the additional spaces in the second line or spaces in first and second planes are orientated parallel to each other.

20. The implantable electrical contact arrangement according to claim 1, wherein:
   upon implantation, the at least one space and material contained therein determines a shape of an area of the implantable electrical contact which applies the contact pressure to the intracorporeal tissue surface.

21. The implantable electrical contact arrangement according to claim 1, wherein:
   the additional spaces are each filled with at least one material distributed along an additional line or are within an additional plane which is separated within a carrier substrate of the film from the straight lines or separated from the first and second planes.

22. The implantable electrical contact arrangement in accordance with claim 1, wherein:
   the modulus of elasticity of the material in the spaces is greater than a modulus of elasticity of the material of the sheet for providing a controlled force; and
   the spaces completely overlap an area of a surface of a carrier substrate of the film so that an area of the carrier substrate containing the electrode is against intracorporal tissue.

23. The implantable electrical contact arrangement in accordance with claim 1, wherein the contact surface is hermetically surrounded by the biocompatible electrical insulating material of a carrier substrate of the film.

\* \* \* \* \*